(12) United States Patent
Owens et al.

(10) Patent No.: US 7,833,194 B2
(45) Date of Patent: *Nov. 16, 2010

(54) CATHETER HAVING INSERTION CONTROL MECHANISM

(75) Inventors: Warren D. Owens, Salt Lake City, UT (US); William R. Hawes, Hudson, OH (US); Cary P. Jenkins, Powell, OH (US); Ken D. Hargett, Pearland, TX (US)

(73) Assignee: CareFusion 202, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/265,488

(22) Filed: Nov. 5, 2008

(65) Prior Publication Data

US 2009/0131915 A1    May 21, 2009

Related U.S. Application Data

(63) Continuation of application No. 10/768,265, filed on Jan. 30, 2004, now Pat. No. 7,458,955, which is a continuation of application No. 09/610,644, filed on Jun. 12, 2000, now Pat. No. 6,702,789, which is a continuation of application No. 09/038,465, filed on Mar. 11, 1998, now abandoned.

(60) Provisional application No. 60/040,678, filed on Mar. 11, 1997.

(51) Int. Cl.
    *A61M 5/00*     (2006.01)

(52) U.S. Cl. .................. 604/117; 604/163; 604/171

(58) Field of Classification Search .................. 604/27, 604/35, 117, 158, 159, 162–163, 164.01, 604/164.08, 171, 172, 264, 523, 528, 533; 128/200.23, 207.14
See application file for complete search history.

(56) References Cited

U.S. PATENT DOCUMENTS 921,368 A     5/1909     Crook (Continued)

FOREIGN PATENT DOCUMENTS

CA     2349724     5/2000

(Continued)

OTHER PUBLICATIONS

"Corpak Gastrostomy Tubes" brochure, copyright 1991, in or before December thereof.

(Continued)

*Primary Examiner*—Theodore J Stigell
(74) *Attorney, Agent, or Firm*—Dicke, Billig & Czaja, PLLC (57) ABSTRACT

The present invention is a catheter having a tube and including mechanisms that provide precision control over insertion and retraction of the catheter tube. The catheter is particularly adapted for introduction into the pulmonary system. The catheter includes an insertion depth control mechanism that acts as a stop and provides a tactile indication to the person inserting the catheter tube that a predetermined position has been reached. The catheter also includes an anti-bunching mechanism to prevent bunching of a protective sleeve disposed around the catheter tube, thereby reducing interference from the sleeve during insertion of the catheter tube.

7 Claims, 4 Drawing Sheets

U.S. PATENT DOCUMENTS

| | | |
|---|---|---|
| 1,074,706 A | 10/1913 | Ferguson |
| 2,084,299 A | 6/1937 | Borden |
| 2,103,050 A | 12/1937 | White |
| 2,412,664 A * | 12/1946 | Wolfram et al. .............. 285/343 |
| 2,941,822 A | 6/1960 | Moecker |
| 3,230,767 A | 1/1966 | Heigl et al. |
| 3,528,869 A | 9/1970 | Dereniuk |
| 3,539,674 A | 11/1970 | Dereniuk et al. |
| 3,556,294 A | 1/1971 | Walck, III et al. |
| 3,645,562 A | 2/1972 | Fandetti et al. |
| 3,667,781 A | 6/1972 | Holbrook |
| 3,675,360 A | 7/1972 | Pierce |
| 3,724,454 A | 4/1973 | Brown |
| 3,731,684 A | 5/1973 | Spiegel |
| 3,820,540 A | 6/1974 | Hirtz et al. |
| 3,826,396 A | 7/1974 | Frassica |
| 3,873,814 A | 3/1975 | Mirdadian |
| 3,944,635 A | 3/1976 | Siegenthaler |
| 3,991,762 A | 11/1976 | Radford |
| 4,020,849 A | 5/1977 | Jackson |
| 4,193,406 A | 3/1980 | Jinotti |
| 4,220,813 A | 9/1980 | Kyle |
| 4,220,814 A | 9/1980 | Kyle et al. |
| 4,240,417 A | 12/1980 | Holever |
| 4,256,437 A | 3/1981 | Brown |
| 4,278,085 A | 7/1981 | Shim |
| 4,299,355 A | 11/1981 | Hakkinen |
| 4,327,723 A | 5/1982 | Frankhouser |
| 4,351,328 A | 9/1982 | Bodai |
| 4,352,951 A | 10/1982 | Kyle |
| 4,416,273 A | 11/1983 | Grimes |
| 4,424,833 A | 1/1984 | Spector et al. |
| 4,427,004 A | 1/1984 | Miller |
| 4,487,604 A | 12/1984 | Iwatschenko et al. |
| 4,510,933 A | 4/1985 | Wendt et al. |
| 4,538,836 A | 9/1985 | Kreutten |
| 4,549,879 A | 10/1985 | Groshong et al. |
| 4,557,261 A | 12/1985 | Reugheimer |
| 4,568,338 A | 2/1986 | Todd |
| 4,595,005 A | 6/1986 | Jinotti |
| 4,636,144 A | 1/1987 | Abe et al. |
| 4,648,396 A | 3/1987 | Raemer |
| 4,658,834 A | 4/1987 | Blankenship et al. |
| 4,671,796 A | 6/1987 | Groshong et al. |
| 4,701,166 A | 10/1987 | Groshong et al. |
| 4,710,171 A * | 12/1987 | Rosenberg ................. 604/117 |
| 4,719,924 A | 1/1988 | Crittenden et al. |
| 4,753,640 A | 6/1988 | Nichols et al. |
| 4,773,901 A | 9/1988 | Norton |
| 4,795,434 A | 1/1989 | Kujawski |
| 4,823,805 A | 4/1989 | Wojcik |
| 4,825,859 A | 5/1989 | Lambert |
| 4,836,199 A | 6/1989 | Palmer |
| 4,838,255 A | 6/1989 | Lambert |
| 4,850,350 A | 7/1989 | Jackson |
| 4,863,442 A | 9/1989 | DeMello et al. |
| 4,872,579 A | 10/1989 | Palmer |
| 4,884,013 A | 11/1989 | Jackson et al. |
| 4,886,067 A | 12/1989 | Palermo |
| 4,909,248 A | 3/1990 | McLennan Anderson |
| 4,913,703 A | 4/1990 | Pasqualucci et al. |
| 4,923,061 A | 5/1990 | Trombley, III |
| 4,932,943 A | 6/1990 | Nowak |
| 4,967,743 A | 11/1990 | Lambert |
| D312,880 S | 12/1990 | Bodai et al. |
| 4,995,387 A | 2/1991 | Jinotti |
| 4,995,863 A | 2/1991 | Nichols et al. |
| 4,998,932 A | 3/1991 | Rosen et al. |
| 5,017,192 A | 5/1991 | Dodge et al. |
| 5,040,543 A | 8/1991 | Badera et al. |
| 5,053,004 A | 10/1991 | Markel et al. |
| 5,059,173 A | 10/1991 | Sacco |
| 5,060,646 A | 10/1991 | Page |
| 5,062,420 A | 11/1991 | Levine |
| 5,077,352 A | 12/1991 | Elton |
| 5,088,486 A | 2/1992 | Jinotti |
| 5,098,378 A | 3/1992 | Piontek et al. |
| 5,104,157 A | 4/1992 | Bahner |
| 5,107,892 A | 4/1992 | Lambert |
| 5,131,407 A | 7/1992 | Ischinger et al. |
| 5,133,345 A * | 7/1992 | Lambert ................. 128/202.16 |
| 5,139,018 A | 8/1992 | Brodsky et al. |
| 5,140,983 A | 8/1992 | Jinotti |
| 5,160,325 A | 11/1992 | Nichols et al. |
| 5,179,174 A | 1/1993 | Elton |
| 5,184,611 A | 2/1993 | Turnbull |
| 5,217,438 A | 6/1993 | Davis et al. |
| 5,217,440 A | 6/1993 | Frassica |
| 5,224,933 A | 7/1993 | Bromander |
| 5,226,423 A | 7/1993 | Tenerz et al. |
| 5,238,218 A | 8/1993 | Mackal |
| 5,255,672 A | 10/1993 | Jinotti |
| 5,265,622 A | 11/1993 | Barbere |
| 5,269,756 A | 12/1993 | Dryden |
| 5,277,177 A | 1/1994 | Page et al. |
| 5,290,585 A | 3/1994 | Elton |
| 5,300,044 A | 4/1994 | Classey et al. |
| 5,309,905 A | 5/1994 | Teves |
| 5,334,153 A | 8/1994 | McIntyre et al. |
| 5,343,857 A | 9/1994 | Schneider et al. |
| 5,349,950 A | 9/1994 | Ulrich et al. |
| 5,365,942 A | 11/1994 | Shank |
| 5,372,592 A | 12/1994 | Gambale |
| 5,375,596 A | 12/1994 | Twiss et al. |
| 5,389,091 A | 2/1995 | Moorehead |
| 5,391,152 A | 2/1995 | Patterson |
| 5,409,459 A | 4/1995 | Gambale |
| 5,417,315 A | 5/1995 | Fukunaga |
| 5,417,664 A | 5/1995 | Felix et al. |
| 5,453,235 A | 9/1995 | Calcote et al. |
| 5,462,527 A | 10/1995 | Stevens-Wright et al. |
| 5,466,230 A | 11/1995 | Davila |
| 5,478,333 A | 12/1995 | Asherman, Jr. |
| 5,484,420 A | 1/1996 | Russo |
| 5,513,637 A | 5/1996 | Twiss et al. |
| 5,603,697 A | 2/1997 | Grundy et al. |
| 5,611,777 A | 3/1997 | Bowden et al. |
| 5,622,169 A | 4/1997 | Golden et al. |
| 5,624,413 A | 4/1997 | Markel et al. |
| 5,637,102 A | 6/1997 | Tolkoff et al. |
| 5,641,443 A | 6/1997 | Calcote et al. |
| 5,642,726 A | 7/1997 | Owens et al. |
| 5,650,759 A | 7/1997 | Hittman et al. |
| RE35,648 E | 11/1997 | Tenerz et al. |
| 5,715,817 A | 2/1998 | Stevens-Wright et al. |
| 5,718,678 A | 2/1998 | Fleming, III |
| 5,727,552 A | 3/1998 | Ryan |
| 5,762,064 A | 6/1998 | Polvani |
| 5,776,111 A | 7/1998 | Tesio |
| 5,779,669 A | 7/1998 | Haissaguerre et al. |
| 5,801,789 A | 9/1998 | Powers et al. |
| 5,830,187 A | 11/1998 | Basta |
| 5,931,811 A | 8/1999 | Haissaguerre et al. |
| 5,935,102 A | 8/1999 | Bowden et al. |
| 5,935,667 A | 8/1999 | Calcote et al. |
| 5,944,732 A | 8/1999 | Raulerson et al. |
| 5,947,953 A | 9/1999 | Ash et al. |
| 6,019,727 A | 2/2000 | Koger et al. |
| 6,033,382 A | 3/2000 | Basta |
| 6,112,111 A | 8/2000 | Glantz |
| 6,129,668 A | 10/2000 | Haynor et al. |
| 6,142,958 A | 11/2000 | Hammarstrom et al. |
| 6,190,382 B1 | 2/2001 | Ormsby et al. |
| 6,226,547 B1 | 5/2001 | Lockhart et al. |

| Patent No. | Date | Inventor |
|---|---|---|
| 6,233,476 B1 | 5/2001 | Strommer et al. |
| 6,245,030 B1 | 6/2001 | DuBois et al. |
| 6,245,098 B1 | 6/2001 | Freeser et al. |
| 6,266,551 B1 | 7/2001 | Osadchy et al. |
| 6,270,902 B1 | 8/2001 | Tedeschi |
| 6,277,100 B1 | 8/2001 | Raulerson et al. |
| 6,298,261 B1 | 10/2001 | Rex |
| 6,312,380 B1 | 11/2001 | Hoek et al. |
| 6,329,488 B1 | 12/2001 | Terry et al. |
| 6,336,906 B1 | 1/2002 | Hammarstrom |
| 6,342,120 B1 | 1/2002 | Basta |
| 6,364,867 B2 | 4/2002 | Wise et al. |
| 6,381,485 B1 | 4/2002 | Hunter et al. |
| 6,447,472 B1 | 9/2002 | Moss |
| 6,461,311 B2 | 10/2002 | DuBois et al. |
| 6,517,481 B2 | 2/2003 | Hoek et al. |
| 6,544,251 B1 | 4/2003 | Crawford |
| 6,551,281 B1 | 4/2003 | Raulerson et al. |
| 6,553,326 B1 | 4/2003 | Kirsch et al. |
| 6,574,498 B1 | 6/2003 | Gilboa |
| 6,579,539 B2 | 6/2003 | Lawson et al. |
| 6,596,401 B1 | 7/2003 | Terry et al. |
| 6,608,688 B1 | 8/2003 | Faul et al. |
| 6,618,612 B1 | 9/2003 | Acker et al. |
| 6,682,519 B1 | 1/2004 | Schon |
| 6,687,531 B1 | 2/2004 | Ferre et al. |
| 6,695,832 B2 | 2/2004 | Schon et al. |
| 6,702,789 B1 * | 3/2004 | Owens et al. ............... 604/264 |
| 6,716,895 B1 | 4/2004 | Terry |
| 6,719,749 B1 | 4/2004 | Schweikert et al. |
| D489,452 S | 5/2004 | Schweikert |
| 6,730,096 B2 | 5/2004 | Basta |
| D491,265 S | 6/2004 | Schweikert |
| 6,749,580 B2 | 6/2004 | Work et al. |
| 6,757,557 B1 | 6/2004 | Bladen et al. |
| 6,772,002 B2 | 8/2004 | Schmidt et al. |
| 6,774,624 B2 | 8/2004 | Anderson et al. |
| 6,786,884 B1 | 9/2004 | DeCant, Jr. et al. |
| 6,796,991 B2 | 9/2004 | Nardeo |
| 6,808,510 B1 | 10/2004 | DiFiore |
| D498,299 S | 11/2004 | Schweikert |
| 6,823,617 B2 | 11/2004 | Nardeo |
| 6,876,196 B1 | 4/2005 | Taulin et al. |
| 6,881,211 B2 | 4/2005 | Schweikert et al. |
| D505,202 S | 5/2005 | Chesnin |
| 6,895,267 B2 | 5/2005 | Panescu et al. |
| 6,908,681 B2 | 6/2005 | Terry et al. |
| 6,911,014 B2 | 6/2005 | Wentling et al. |
| 6,916,051 B2 | 7/2005 | Fisher |
| 6,926,721 B2 | 8/2005 | Basta |
| 6,939,328 B2 | 9/2005 | Raulerson |
| 6,969,381 B2 | 11/2005 | Voorhees |
| 6,980,921 B2 | 12/2005 | Anderson et al. |
| 6,991,625 B1 | 1/2006 | Gately et al. |
| D515,211 S | 2/2006 | Chesnin |
| 7,004,938 B2 | 2/2006 | Ormsby et al. |
| 7,015,859 B2 | 3/2006 | Anderson |
| 7,018,374 B2 | 3/2006 | Schon et al. |
| 7,096,148 B2 | 8/2006 | Anderson et al. |
| 7,158,754 B2 | 1/2007 | Anderson |
| 7,197,354 B2 | 3/2007 | Sobe |
| 7,273,473 B2 * | 9/2007 | Owens et al. ............... 604/264 |
| 7,458,955 B2 * | 12/2008 | Owens et al. ............... 604/117 |
| 2002/0032411 A1 | 3/2002 | Basta |
| 2003/0066218 A1 | 4/2003 | Schweikert |
| 2003/0125725 A1 | 7/2003 | Woodard et al. |
| 2004/0087996 A1 | 5/2004 | Gambale et al. |
| 2004/0092863 A1 | 5/2004 | Raulerson et al. |
| 2004/0097903 A1 | 5/2004 | Raulerson et al. |
| 2004/0098020 A1 | 5/2004 | Nardeo |
| 2004/0122416 A1 | 6/2004 | Schweikert |
| 2004/0122418 A1 | 6/2004 | Voorhees |
| 2004/0195131 A1 | 10/2004 | Spolidoro |
| 2004/0230169 A1 | 11/2004 | Felix et al. |
| 2004/0249337 A1 | 12/2004 | DiFiore |
| 2004/0249338 A1 | 12/2004 | DeCant, Jr. et al. |
| 2004/0249349 A1 | 12/2004 | Wentling |
| 2005/0000844 A1 | 1/2005 | Schweikert |
| 2005/0038453 A1 | 2/2005 | Raulerson |
| 2005/0043684 A1 | 2/2005 | Basta |
| 2005/0049572 A1 | 3/2005 | Schweikert et al. |
| 2005/0049628 A1 | 3/2005 | Schweikert et al. |
| 2005/0085765 A1 | 4/2005 | Voorhees |
| 2005/0096585 A1 | 5/2005 | Schon et al. |
| 2005/0107770 A1 | 5/2005 | Schweikert et al. |
| 2005/0120523 A1 | 6/2005 | Schweikert |
| 2005/0124970 A1 | 6/2005 | Kunin |
| 2005/0137527 A1 | 6/2005 | Kunin |
| 2005/0137580 A1 | 6/2005 | Raulerson et al. |
| 2005/0192545 A1 | 9/2005 | Voorhees et al. |
| 2005/0222593 A1 | 10/2005 | Markel et al. |
| 2005/0228370 A1 | 10/2005 | Sterzer et al. |
| 2005/0234369 A1 | 10/2005 | Voorhees |
| 2005/0261665 A1 | 11/2005 | Voorhees et al. |
| 2006/0015072 A1 | 1/2006 | Raulerson |
| 2006/0015130 A1 | 1/2006 | Voorhees et al. |
| 2006/0030827 A1 | 2/2006 | Raulerson |
| 2006/0047267 A1 | 3/2006 | Gately |
| 2006/0047268 A1 | 3/2006 | Stephens |
| 2006/0064072 A1 | 3/2006 | Gately et al. |
| 2006/0142752 A1 | 6/2006 | Ormsby et al. |
| 2006/0184011 A1 | 8/2006 | Macaulay et al. |

FOREIGN PATENT DOCUMENTS

| | | |
|---|---|---|
| CA | 2389227 | 5/2001 |
| CA | 2407461 | 3/2002 |
| DE | 2265373 | 8/1972 |
| DE | 2238722 | 2/1973 |
| DE | 2556878 | 6/1977 |
| DE | 3247548 | 7/1983 |
| DE | 3247576 | 7/1983 |
| DE | 3334174 | 9/1983 |
| DE | 3434752 | 4/1985 |
| DE | 3444807 | 6/1985 |
| DE | 3610270 | 3/1986 |
| DE | 3645161 | 3/1992 |
| DE | 3884020 | 3/1994 |
| DE | 69102293 | 10/1994 |
| DE | 68918888 | 11/1994 |
| DE | 69209707 | 10/1996 |
| DE | 69216468 | 5/1997 |
| DE | 69216513 | 5/1997 |
| DE | 3752245 | 2/1999 |
| DE | 69425034 | 3/2001 |
| DE | 68918632 | 10/2003 |
| DE | 69332716 | 10/2003 |
| DE | 69730135 | 7/2005 |
| DE | 69733010 | 2/2006 |
| EP | 125843 | 11/1984 |
| EP | 125844 | 11/1984 |
| EP | 259945 | 3/1988 |
| EP | 263645 | 4/1988 |
| EP | 274412 | 7/1988 |
| EP | 282143 | 9/1988 |
| EP | 307162 | 3/1989 |
| EP | 347035 | 12/1989 |
| EP | 382974 | 8/1990 |
| EP | 421650 | 4/1991 |
| EP | 440427 | 8/1991 |
| EP | 454293 | 10/1991 |
| EP | 456342 | 11/1991 |
| EP | 476807 | 3/1992 |
| EP | 502664 | 9/1992 |
| EP | 513991 | 11/1992 |
| EP | 537136 | 4/1993 |

| | | |
|---|---|---|
| EP | 773810 | 5/1997 |
| EP | 839547 | 5/1998 |
| EP | 1310514 | 5/2003 |
| EP | 1313527 | 5/2003 |
| EP | 1477202 | 11/2004 |
| GB | 891754 | 3/1962 |
| JP | 1104250 | 4/1989 |
| JP | 3051052 | 3/1991 |
| JP | 4224766 | 8/1992 |
| JP | 5245209 | 9/1993 |
| NZ | 234127 | 10/1992 |
| WO | 94/21318 | 9/1944 |
| WO | 89/05671 | 6/1989 |
| WO | 91/01772 | 2/1991 |
| WO | 98/18515 | 5/1998 |
| WO | 99/44668 | 9/1999 |
| WO | 00/12165 | 3/2000 |
| WO | 00/38567 | 7/2000 |
| WO | 01/74434 | 10/2001 |
| WO | 01/89603 | 11/2001 |
| WO | 02/13899 | 2/2002 |
| WO | 02/18004 | 3/2002 |
| WO | 03/047636 | 6/2003 |
| WO | 2004/041329 | 5/2004 |
| WO | 2004/075962 | 9/2004 |
| WO | 2004/087249 | 10/2004 |
| WO | 2005/035040 | 4/2005 |
| WO | 2005/065761 | 7/2005 |
| WO | 2005/084741 | 9/2005 |

OTHER PUBLICATIONS

"Sherlock™ Tip Locatio System 510(k) Summary of Safety and Effectiveness 21 CFR 807.92(a)," submitted by Bard Access Systems, Inc. (BAS) [Wholly owned Subsidiary of C.R. Bard, Inc.] on Feb. 9, 2006.
"Stent," [online] [retrieved on Sep. 5, 2006]. Retrieved from the Internet at <URL: http://www.guidant.com/condition/images/030Stent.jpg>.
1P Series Catalog, prior to Jan. 13, 2005.
Biosense Webster, A Johnson & Johnson Company, CARTO™ EP Navigation System, [online] [printed from the Internet on Oct. 23, 2002] <URL: http://www.biosensewebster.com/US/products_carton_av.htm>.
Biosense Webster, A Johnson & Johnson Company, CUSOTMCATH™ Program, [online] [printed from the Internet on Oct. 23, 2002] <URL: http://www.biosensewebster.com/US/products_carton_av.htm>.
CARTO™ EP Navigation System, [online] [printed from the Internet on Oct. 23, 2002] <URL: http://www.biosensewebster.com/US/products_carton_av.htm>.
CF-Q160AL innoflex™, Olympus® Focus on Life, [online] [printed from the Internet on Oct. 22, 2002] <URL: http://www.olympusamerica.com/msg_section>.
CF-Q160S, EVIS EXERA™, Olympus® Focus on Life, [online] [printed from the Internet on Oct. 22, 2002] <URL: http://www.olympusamerica.com/msg_section>.
Corpak Enteral Feeding Pump Model 300D, Corpak, Inc., 1989 on or before December thereof.
Corpak Enteral Feeding Pump Model VTR 300, Corpak, Inc., 1987 on or before December thereof.
Corpak's Proven Enteral Delivery System—Complete and Versatile, advertisement, Corpak Company, 1986 on or before Dec. thereof.
Department of Health and Human Services, Navi-Star Diagnostic/Ablation Deflectable Tip Catheter, Food and Drug Administration, Jun. 15, 2000.
Enteral Systems Brochure, Corpak, Inc., Aug. 1992.
EVIS 140 Series, [online] [printed from the Internet on Oct. 22, 2002] <URL: http://www.olympus.co.jp>.
EVIS 240 Series, [online] [printed from the Internet on Oct. 22, 2002] <URL: http://www.olympus.co.jp>.

Extender cable graphic, manufactured by LEMO USA Inc., distributed and sold by HLC Ltd. as of Jul. 29, 2002.
Flexiflo® Companion® Enteral Nutrition Pump Operating Manual, Ross Laboratories, 1987 on or before December thereof.
Flexiflo® QUANTUM™ Enteral Pump Operating Manual, Ross Laboratories, 1992 on or before December thereof.
Flexiflo-III Enteral Nutrition Pump Operating Manual, Ross Laboratories, 1985 on or before December thereof.
Flow Through Stylet Connector, Corpak MedSystems, Aug. 19, 1987.
FMN Connector Connectors for FFC, written by JST, pp. 390-391, prior to Jan. 13, 2005.
GIF-N30 Fiberscope, Olympus® focus on Live, [online] [printed from the Internet on Oct. 22, 2002] <URL: http://www.olympusamerica.com/msg_section>.
GIF-XP160, SlimSIGHT™, Olympus® Focus on Life, [online] [printed from the Internet on Oct. 22, 2002] <URL: http://www.olympusamerica.com/msg_section>.
kangaroo® 324 Feeding Pump Operating Manual, Sherwood Medical Company, 1991 on or before December thereof.
KM-80 Enteral Feeding Pump Operating Instructions, O'Brien, available prior to 1986 on or before December thereof.
LEMO's Push-Pull Self-Latching Connection System, p. 5, LEMO USA Inc., prior to Jan. 13, 2005.
Lucent® Medical Systems, Adding Intelligence to Indwelling Devices, [online] [printed from the Internet on Oct. 23, 2002] <URL: http://www.lucentmedical.com/overview2.htm.>.
Lucent® Medical Systems, Enteral Feeding Tubes, [online] [printed from the Internet on Oct. 23, 2002] <URL: http://www.lucentmedical.com/et.htm>.
Lucent® Medical Systems, The LMS—Zortran® [online] [printed from the Internet on Oct. 23, 2002] <URL:http://www.lucentmedical.com/zortran.htm>.
Multiple Lesion™ FFR of Serial Tandem Lesions, Florence Medical [online] [printed from the Internet on Oct. 22, 2002] <URL:http://www.florencemedical.com>.
Navi-Staro® diagnostic/Ablation Deflectable Tip Catheter, U.S. Food and Drug Administration—Center for Devices and Radiological Health, printed in 2002, on or before the month of December thereof.
News from NAVION™ [online] [printed from the Internet on Oct. 23, 2002] <URL: http://www.navionbiomedical.com/system.htm>.
Olympus Medical Endoscope & Surgical Products, Olympus, [online] [printed from the Internet on Oct. 17, 2002] <URL:http://www.olympus.co.jp/LineUp/Endoscope/indexE.html>.
Olympus Medical Endoscope & Surgical Products, Olympus, [online] [printed from the Internet on Oct. 22, 2002] <URL: http://www.olympus.co.jp/en/mesg/endoscope>.
Research in Catheter and Tube Placement, [online] [printed from the Internet on October 23, 2002] <Url: http://www.navionbiomedical.com/system.htm>.
Selection of contact types, p. 9, LEMO USA Inc., prior to Jan. 13, 2005.
SmartFlow® Family of Product, Simultaneous CFR/FFR™ [online] [printed from the Internet on Oct. 22, 2002] <URL: http://www.florencemedical.com/aboutFlorence/history.htm>.
The Navion™ BioNavigation System, [online] [printed from the Internet on Oct. 23, 2002] <URL: http://www.navionbiomedical.com/system.htm>.
"NAVIGATØR®, " VIASYS®Healthcare, [online] [retrieved on Aug. 30, 2006]. Retrieved from <file://C:\DOCUME~1/rys.BBL{cube root}LOCALS~1{cube root}Temp{cube root}PDDJQIEU.htm>.
NAV PICC™ and NAV PRØ-PICC™, [online] [retrieved on Aug. 30, 2006]. Retrieved from <URL: http://www.viasyshealthcare.com/prod_serv/prodDetail.aspx?config=ps_prodDtl&prodID=322 >.
US 5,646,065, 07/1997, Shapiro et al. (withdrawn)

* cited by examiner

CATHETER HAVING INSERTION CONTROL MECHANISM

PRIORITY CLAIM

This application is a continuation of U.S. application Ser. No. 10/768,265, filed Jan. 30, 2004, now U.S. Pat. No. 7,458,955, issued on Dec. 2, 2008, which is a continuation of and claims the benefit of U.S. application Ser. No. 09/610,644, file Jun. 12, 2000 now U.S. Pat. No. 6,702,789, issued Mar. 9, 2004, which is a continuation of U.S. application Ser. No. 09/038,465, filed Mar. 11, 1998, now abandoned, which claims priority to U.S. Provisional Patent Application Ser. No. 60/040,678, filed Mar. 11, 1997.

CROSS-REFERENCE TO RELATED APPLICATION

This application is related to commonly-owned U.S. application Ser. No. 10/768,852, now U.S. Pat. No. 7,273,473, issued Sep. 25, 2007.

TECHNICAL FIELD

The present invention relates to medical catheters, and more particularly to catheters used to remove substances from, or introduce substances into, the pulmonary system or gastrointestinal tract of a patient.

BACKGROUND OF THE INVENTION

In certain medical treatment situations, catheters must be precisely introduced into a patient's pulmonary system or gastrointestinal tract for various functions. For example, a patient may require involuntary aspiration of secretions from the patient's lungs. In this situation, a suction catheter can be introduced into the patient's airway and lungs to remove the secretions via suction through the catheter. In addition, a patient may require introduction of various substances into the body through such catheters. For example, a patient may require the introduction of a lavage solution into the lungs to loosen secretions without interfering with ventilation.

Respiratory distress frequently occurs in infants and small children, especially prematurely born infants. Premature infants may require repeated pulmonary intervention. When an infant- or small child is unable to effectively breathe on their own, intubation and involuntary ventilation is provided via an endotracheal tube. In caring for infant patients, it is necessary to periodically suction out secretions that would otherwise accumulate in the infant's lungs. This requires periodic involuntary removal of secretions from the lungs via a small suction catheter tube without injury to the lungs. Suctioning and/or introduction of therapeutic substances may take place intermittently during ventilation.

Suctioning is generally accomplished by introducing and advancing one end of a flexible suction catheter tube into the endotracheal tube and applying suction to the other end of the catheter tube. To reduce the extent of airway occlusion, the catheter tube is typically withdrawn from the endotracheal tube when the catheter is not in use.

Before the catheter tube is advanced through the endotracheal tube, the catheter tube may be "exposed" within the catheter assembly. However, many catheters include a flexible sleeve that covers the span of tubing between the fittings of a catheter to avoid the introduction of microbial pathogens during intubation. The sleeve encloses the catheter tube and preserves the sterility of the tube in a closed system. The sleeve remains fixed to the fittings of the catheter. The sleeve is flexible so that the catheter can be advanced by manipulating the catheter from the outside of the sleeve. Thus, the catheter may be intermittently introduced without breaking the sterile field created by the sleeve around the catheter.

Precise control over the placement of the catheter tube is also required to reduce the risk of injury during placement. The catheter must be advanced far enough to effectively reach the lungs without damaging tissue by overextension of the catheter. The use of a catheter having a protective sleeve further impacts control over the catheter during placement. As the catheter is fully advanced, the sleeve may bunch, making precise control more difficult. Thus, there is a need for a catheter having a mechanism for controlling insertion depth while preventing bunching of the protective sleeve as the catheter is inserted.

SUMMARY OF THE INVENTION

The present invention is a catheter having a tube and including mechanisms that provide precision control over insertion and retraction of the catheter tube. The catheter is particularly adapted for introduction into the pulmonary system. The catheter includes an insertion depth control mechanism that acts as a stop and provides a tactile indication to the person inserting the catheter tube that a predetermined position has been reached. The catheter also includes an anti-bunching mechanism to prevent bunching of a protective sleeve disposed around the catheter tube, thereby reducing interference from the sleeve during insertion of the catheter tube.

In one embodiment, the insertion depth control mechanism comprises an insertion control member that is adjustably positioned on the catheter tube. The insertion control member includes a releasable catch to permit adjustment of its position along the catheter tube. When placed in a predetermined position that corresponds to a predetermined insertion depth, the insertion control member acts as a stop against a connector or other form attached to the tube. When the insertion control member reaches the connector or form during insertion of the tube, it bumps against the connector or form and stops the advancement of the catheter tube at a predetermined length. This resistance provides a tactile response, or feel, to a person inserting the catheter, which indicates that the catheter tube has been inserted to the predetermined depth. The insertion control member can comprise a number of different shapes.

In one embodiment, the anti-bunching mechanism comprises a sleeve spreader including an outer surface concentrically disposed around the catheter tube and adjacent a tube opening of a distal connector attached to the catheter. The sleeve spreader deflects the sleeve away from the tube opening of the distal connector and prevents it from bunching at the tube opening, thereby avoiding interference with advancement of the catheter tube.

DETAILED DESCRIPTION OF THE INVENTION

While the present invention will be described fully hereinafter with reference to the accompanying drawings, in which a particular embodiment is shown, it is to be understood at the outset that persons skilled in the art may modify the invention herein described while still achieving the desired result of this invention. Accordingly, the description which follows is to be understood as a broad informative disclosure directed to persons skilled in the appropriate arts and not as limitations of the present invention.

Figure 1:
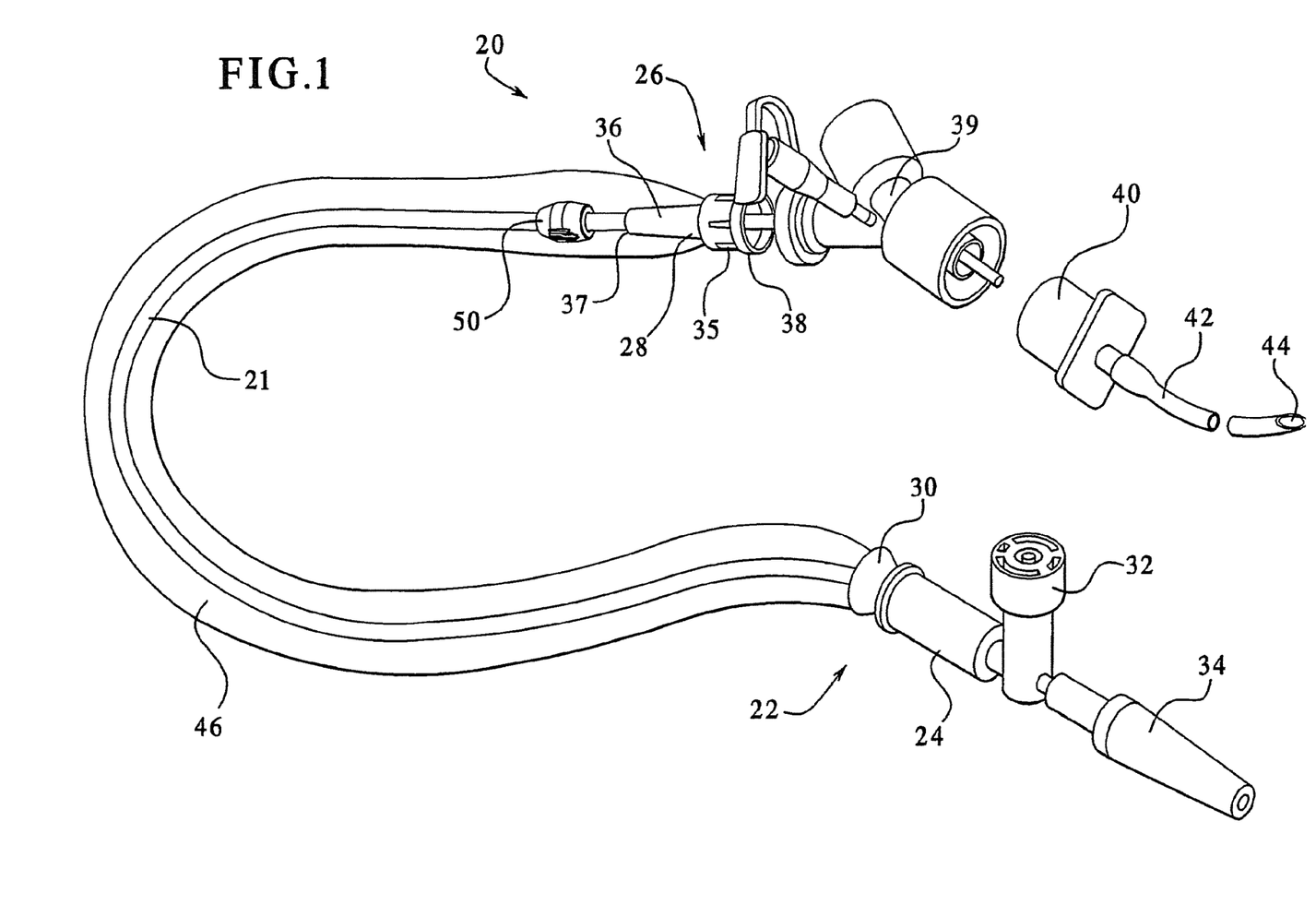
FIG. 1 is a perspective view of a catheter of the present invention including a connector for a ventilation apparatus.

FIG. 1 is an exploded view of a suction catheter 20 and associated attachments for use in a typical ventilator circuit. The suction catheter 20 incorporates an insertion depth control mechanism and an anti-bunching mechanism as described herein. The suction catheter 20 includes a catheter tube 21, a proximal end 22 having a proximal connector assembly 24, and a distal end 26 having a distal spreader connector 28. The proximal connector assembly 24 includes a sleeve collar 30, a vacuum valve 32, and a terminal connector 34. The distal spreader connector 28 includes a sleeve collar 35 and a generally cone-shaped extension 36 that extends toward the proximal end 22 of the catheter 20. The cone-shaped extension includes a tube aperture 37. The catheter tube 21 passes through the tube aperture 37. The distal spreader connector 28 has a fitting 38 that can be connected to an adapter device 39. To complete the ventilation circuit, the adapter device 39 is connected to a conventional ventilation adapter 40 that includes an endotracheal tube 42 having an end opening 44. Other components may be used in connection with the suction catheter 20 without departing from the present invention, such as those disclosed in U.S. Pat. No. 5,642,726, which is incorporated herein by reference.

The catheter tube 21 of the suction catheter 20 is surrounded by a flexible external sleeve 46 that spans from the proximal connector assembly 24 to the distal spreader connector 28, as shown in FIG. 1. The external sleeve 46 is attached to the proximal connector assembly 24 within the sleeve collar 30 and the distal spreader connector 28 within the sleeve collar 35. The sleeve 46 may be banded to the sleeve collars 30 and 35 or adhered thereto. The external sleeve 46 encloses the catheter tube 21 to preserve its sterility during use in a closed system.

During intubation, the catheter tube 21 of the suction catheter 20 is introduced into the endotracheal tube 42 through the distal spreader connector 28 and the adapter device 39 and advanced to a predetermined depth. The depth of insertion is controlled by an insertion control member 50. During insertion of the catheter tube 21, the insertion control member 50 acts as a stop against the cone-shaped extension 36 of the distal spreader connector 28, thus stopping the advancement of the catheter at a predetermined length. The insertion control member 50 also provides a tactile feel to the operator when it bumps against the extension 36, thereby signaling to the operator that the proper depth has been reached.

Figure 2A:
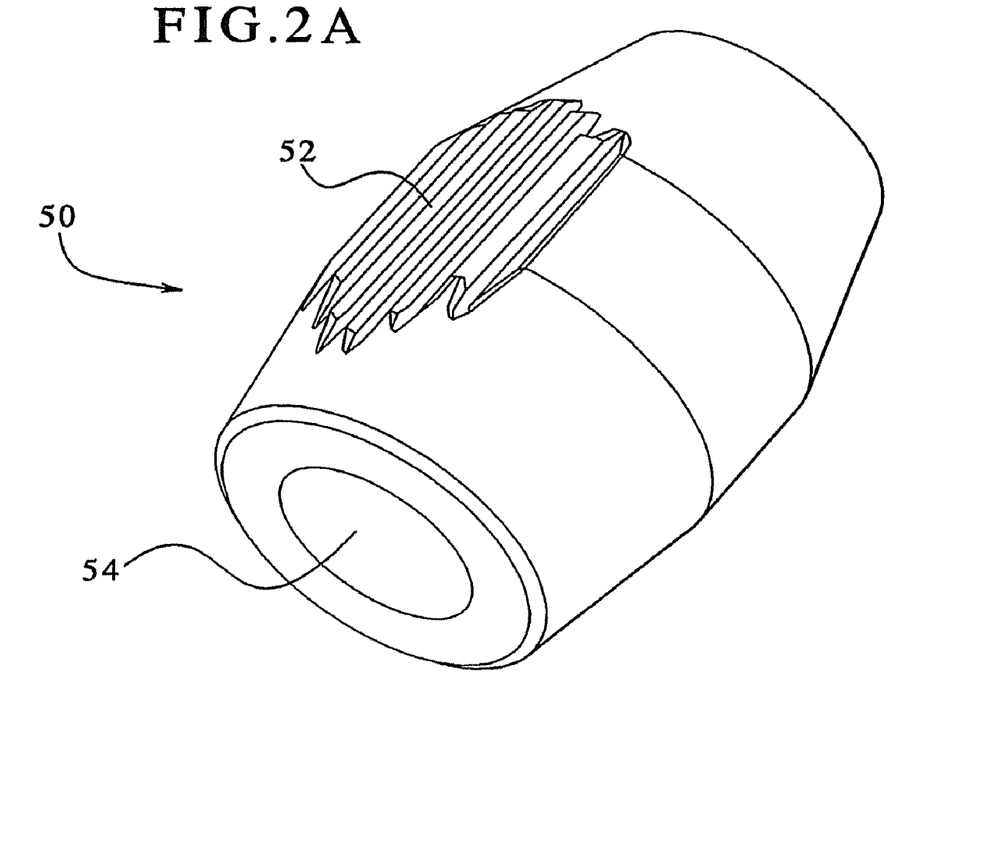
FIG. 2A is a perspective view of a first embodiment of an insertion control member of the present invention.
Figure 2B:
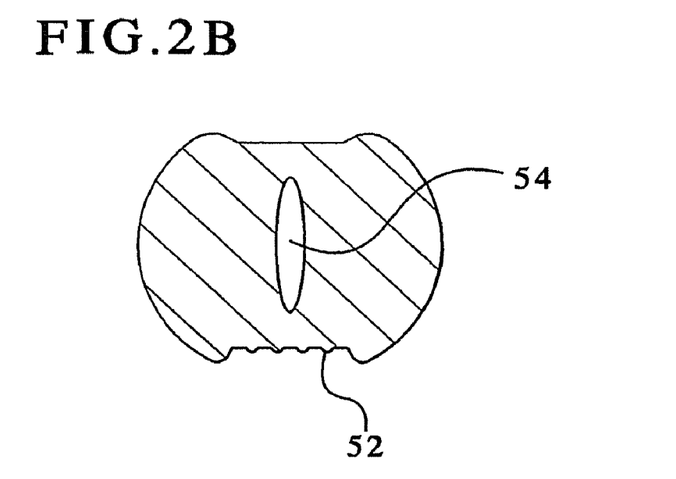
FIG. 2B is a cross-sectional view of the insertion control member shown in FIG. 2A taken transversely through the center of the insertion control member.

In the embodiment depicted in FIG. 1, the insertion control member 50 has a generally barreled shape as shown in FIGS. 2A and 2B. The insertion control member 50 includes two flattened grip portions 52 and a tube passage 54. As shown in FIG. 2B, the tube passage 54 has an elongated cross-section near the center of the insertion control member 50. The catheter tube 21 passes through the tube passage 54 and the elongated configuration of the tube passage 54 grips the catheter tube 21 to hold the insertion control member 50 at a predetermined position along the catheter tube 21. The catheter tube 21 may include indicia to help facilitate depth adjustment of the catheter tube 21 via the insertion control member 50. The position of the insertion control member 50 can be adjusted by an operator pinching the insertion control member 50 at the flattened grip portions 52 to flex the elongated cross-section of the of the tube passage 54 to form a relatively wider cross-section. The wider cross-section allows the operator to slide the insertion control member 50 to a new position on the catheter tube 21. When the insertion control member 50 is repositioned, the operator releases the flattened grip portions 52 so that the cross-section of the tube passage 54 returns to its elongated configuration. Alternatively, the cross-section of the tube passage 54 may include other features to help grip the catheter tube 21, such as teeth or other projections.

Figure 3:
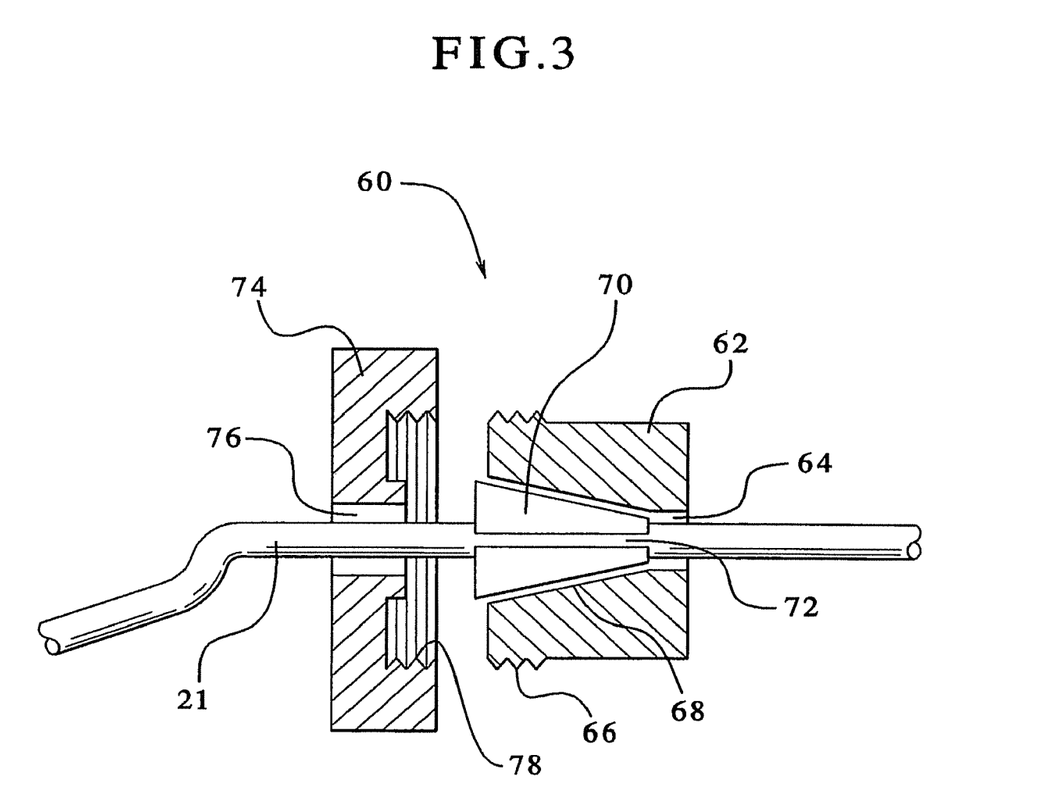
FIG. 3 is a cross-sectional side view of a second embodiment of an insertion control member of the present invention.

FIG. 3 shows an alternate embodiment in the form of an insertion control assembly 60. The insertion control assembly 60 includes a threaded sleeve 62 having a thru-hole 64 and external threads 66 on one end of the sleeve 62. The thru-hole 64 has a tapered surface 68 that accepts a tapered collet 70, as shown in FIG. 3. The tapered collet 70 includes a channel 72 therethrough. A mating nut 74 includes a thru-hole 76 and internal threads 78 that are adapted to engage the external threads 66 of the threaded sleeve 62. The catheter tube 21 passes through the thru-hole 64 of the threaded sleeve 62, the channel 72 of the tapered collet 70, and the thru-hole 76 of the mating nut 74. When the threaded sleeve 62 and the mating nut 74 are engaged and tightened, the threaded sleeve 62 deflects and compresses the tapered collet 70 around the catheter tube 21, thereby securing the insertion control assembly 60 to the catheter tube 21.

Figure 4:
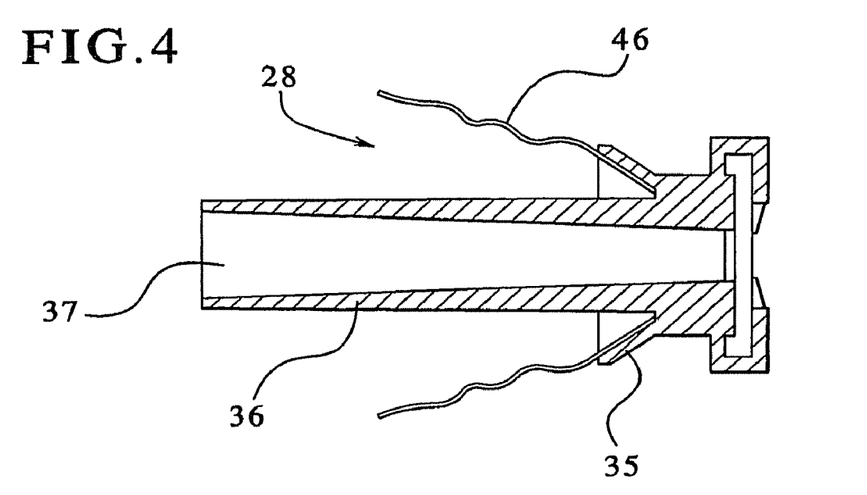
FIG. 4 is a cross-sectional view of a sleeve spreader of the catheter shown in FIG. 1.

FIG. 4 is a cross-sectional view of the distal spreader connector 28 shown in FIG. 1. As the catheter tube 21 is advanced through the distal spreader connector 28 and the adapter device 39, the external sleeve 46 begins to bunch up near the distal spreader connector 28. The cone-shaped extension 36 of the distal spreader connector 28 acts to spread or deflect the sleeve 46 as the catheter tube 21 is advanced and prevent the sleeve 46 from interfering with the tube opening or aperture 37 of the extension 36 of the distal spreader connector 28. The sleeve 46 is attached to the distal spreader connector 28 between the collar 35 and the extension 36, as shown in FIG. 4.

Figure 5A:
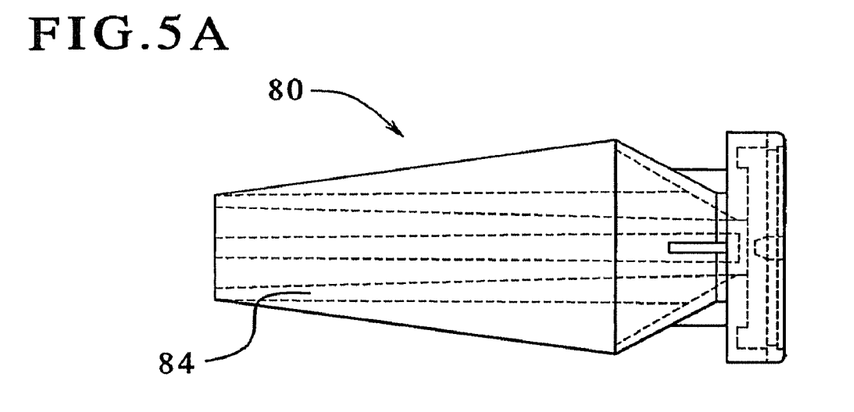
FIG. 5A is an elevational view of a second embodiment of a sleeve spreader of the present invention.
Figure 5B:
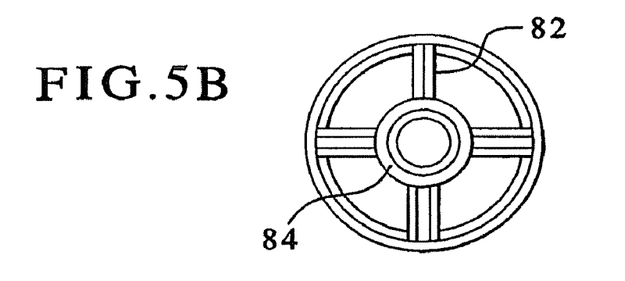
FIG. 5B is a cross-sectional view of the sleeve spreader shown in FIG. 5A.

FIGS. 5A and 5B show an alternate embodiment in the form of a distal spreader connector 80. In this embodiment, the distal spreader connector 80 includes a set of four tapered ribs 82 that extend from an extension 84. The tapered ribs 82 provide further deflection and spreading of the sleeve 46 as the catheter tube 21 is advanced. Accordingly, the distal spreader connector 80 deflects the sleeve adjacent to the tube opening of the distal spreader connector.

While the specific embodiments have been illustrated and described, numerous modifications come to mind without significantly departing from the spirit of the invention and the scope of protection is only limited by the scope of the accompanying claims.

What is claimed is:

1. A catheter assembly comprising:
   a proximal end, a distal end, a catheter tube extending between the proximal end and the distal end;

a proximal connector positioned at the proximal end, the proximal connector being configured to be coupled to a medical device;

a distal connector positioned at the distal end, the distal connector configured to be coupled to a medical device, the distal connector comprising a sleeve collar and an extension extending from the sleeve collar toward the proximal end such that the extension is positioned between the sleeve collar and the proximal end, the extension defining a tube aperture, wherein the catheter tube is movable through the distal connector;

an insertion control member adjustably carried on the catheter tube and configured to provide a tactile indication to a user that a predetermined position of the catheter tube has been reached as the catheter tube is advanced through the distal connector, the insertion control member further including two opposed flattened grip portions and a tube passage with an elongated cross-section, the elongated cross-section of the tube passage enabling the insertion control member to grip the catheter tube, wherein when the grip portions are pinched together by the user the elongated cross-section becomes wider so that the user can slide the insertion control member along the catheter tube and wherein the release of the grip portions causes the tube passage to return to the elongated cross-section so that the catheter tube is gripped again; and a flexible sleeve connected to the sleeve collar and proximal connector and disposed around the catheter tube and extension to preserve the sterility of the catheter tube, the extension of the distal connector configured to deflect the flexible sleeve to prevent the sleeve from interfering with the tube aperture of the distal connector.

2. The catheter assembly of claim 1, wherein the extension is generally cone-shaped.

3. The catheter assembly of claim 1, wherein the extension includes a set of ribs extending away from the extension such that the ribs provide further deflection of the flexible sleeve.

4. The catheter assembly of claim 1, wherein the distal connector is configured to be coupled to an adapter device and the adapter device is configured to be coupled to a ventilation adapter and endotracheal tube.

5. A catheter assembly comprising:
a proximal end, a distal end, a catheter tube extending between the proximal end and the distal end;
a proximal connector positioned at the proximal end, the proximal connector being configured to be coupled to a medical device;
a distal connector positioned at the distal end, the distal connector configured to be coupled to a medical device, the distal connector comprising a sleeve collar and an extension extending from the sleeve collar toward the proximal end such that the extension is positioned between the sleeve collar and the proximal end, the extension defining a tube aperture, wherein the catheter tube is movable through the distal connector;
an insertion control assembly adjustably carried on the catheter tube and configured to provide a tactile indication to a user that a predetermined position of the catheter tube has been reached as the catheter tube is advanced through the distal connector, the insertion control assembly comprising a threaded sleeve, a mating nut engaging the threaded sleeve and a collet disposed between the threaded sleeve and the mating nut such that tightening of the threaded sleeve and mating nut compresses the collet to secure the insertion control assembly to the catheter tube; and
a flexible sleeve disposed around the insertion control assembly and the catheter tube to preserve the sterility of the catheter tube, the flexible sleeve extending between the proximal and distal connectors, the extension of the distal connector configured to deflect the flexible sleeve to prevent the sleeve from interfering with the tube aperture of the distal connector.

6. The catheter assembly of claim 5, wherein the collet is tapered and defines a channel therethrough for receiving the catheter tube.

7. The catheter assembly of claim 5, wherein the distal connector is configured to be coupled to an adapter device and the adapter device is configured to be coupled to a ventilation adapter and endotracheal tube.

* * * * *

UNITED STATES PATENT AND TRADEMARK OFFICE
CERTIFICATE OF CORRECTION

| | |
|---|---|
| PATENT NO. | : 7,833,194 B2 |
| APPLICATION NO. | : 12/265488 |
| DATED | : November 16, 2010 |
| INVENTOR(S) | : Warren D. Owens et al. |

It is certified that error appears in the above-identified patent and that said Letters Patent is hereby corrected as shown below:

Page 2, Column 2 (U.S. Patent Documents), line 8, delete "5,107,892" and insert in place thereof --5,107,829--.

Page 2, Column 2 (U.S. Patent Documents), line 60, delete "5,801,789" and insert in place thereof --5,810,789--.

Page 2, Column 2 (U.S. Patent Documents), line 61, delete "5,830,187" and insert in place thereof --5,830,184--.

Page 4, Column 1 (Other Publications), line 1, delete "Locatio" and insert in place thereof --Location--.

Page 4, Column 2 (Other Publications), line 31, delete "Zortran®" and insert in place thereof --Zortran™--.

Page 4, Column 2 (Other Publications), line 37, delete "Navi-Staro®" and insert in place thereof --NAVI-STAR®--.

Page 4, Column 2 (Other Publications), line 62-63, delete "BBL{cube root}LOCALS~1{cube root}Temp{cube root}PDDJQIEU.htm>." and insert in place thereof --BBL\LOCALS~1\Temp\PDDJQIEU.htm>.--.

Signed and Sealed this
Twenty-fifth Day of January, 2011

David J. Kappos
*Director of the United States Patent and Trademark Office*